US006872302B2

(12) United States Patent
Aste

(10) Patent No.: US 6,872,302 B2
(45) Date of Patent: Mar. 29, 2005

(54) CHROMATOGRAPHIC APPARATUS

(75) Inventor: Giacomo Aste, Genoa (IT)

(73) Assignee: Alfatech S.p.A. (IT)

( * ) Notice: Subject to any disclaimer, the term of this patent is extended or adjusted under 35 U.S.C. 154(b) by 10 days.

(21) Appl. No.: 10/387,861

(22) Filed: Mar. 14, 2003

(65) Prior Publication Data

US 2003/0173279 A1 Sep. 18, 2003

(30) Foreign Application Priority Data

Mar. 15, 2002 (IT) ..................................... GE2002A0023

(51) Int. Cl.[7] ............................................. B01D 15/08
(52) U.S. Cl. ...................... 210/198.2; 210/656; 96/101
(58) Field of Search ................................ 210/635, 656, 210/659, 232, 238, 282; 96/101, 106

(56) References Cited

U.S. PATENT DOCUMENTS

| 3,453,811 A | | 7/1969 | Crowley | .................. 210/198.2 |
|---|---|---|---|---|
| 4,250,035 A | * | 2/1981 | McDonald et al. | ....... 210/198.2 |
| 4,354,932 A | | 10/1982 | McNeil | .................... 210/198.2 |
| 4,769,141 A | | 9/1988 | Couillard | ................. 210/198.2 |
| 4,891,133 A | | 1/1990 | Colvin, Jr. | ............... 210/198.2 |
| 4,894,152 A | | 1/1990 | Colvin, Jr. et al. | ...... 210/198.2 |
| 5,601,708 A | | 2/1997 | Leavesley | ................ 210/198.2 |
| 5,651,885 A | | 7/1997 | Schick | .................... 210/198.2 |

FOREIGN PATENT DOCUMENTS

| DE | 41 18 501 | 12/1992 | .............. 210/198.2 |
|---|---|---|---|
| EP | 0 754 085 | 1/1997 | .............. 210/198.2 |
| EP | 0 762 118 | 3/1997 | .............. 210/198.2 |
| FR | 2 681 138 | 3/1993 | .............. 210/198.2 |

* cited by examiner

Primary Examiner—Ernest G. Therkorn
(74) Attorney, Agent, or Firm—Stites & Harbison PLLC; Marvin Petry

(57) ABSTRACT

An apparatus for pressurizing a removable chromatographic cartridge, comprises radial pressure means acting onto the side surface of the chromatographic cartridge, and axial pressure means acting onto the ends of the chromatographic cartridge. During use, the axial and radial pressure means are simultaneously active.

23 Claims, 6 Drawing Sheets

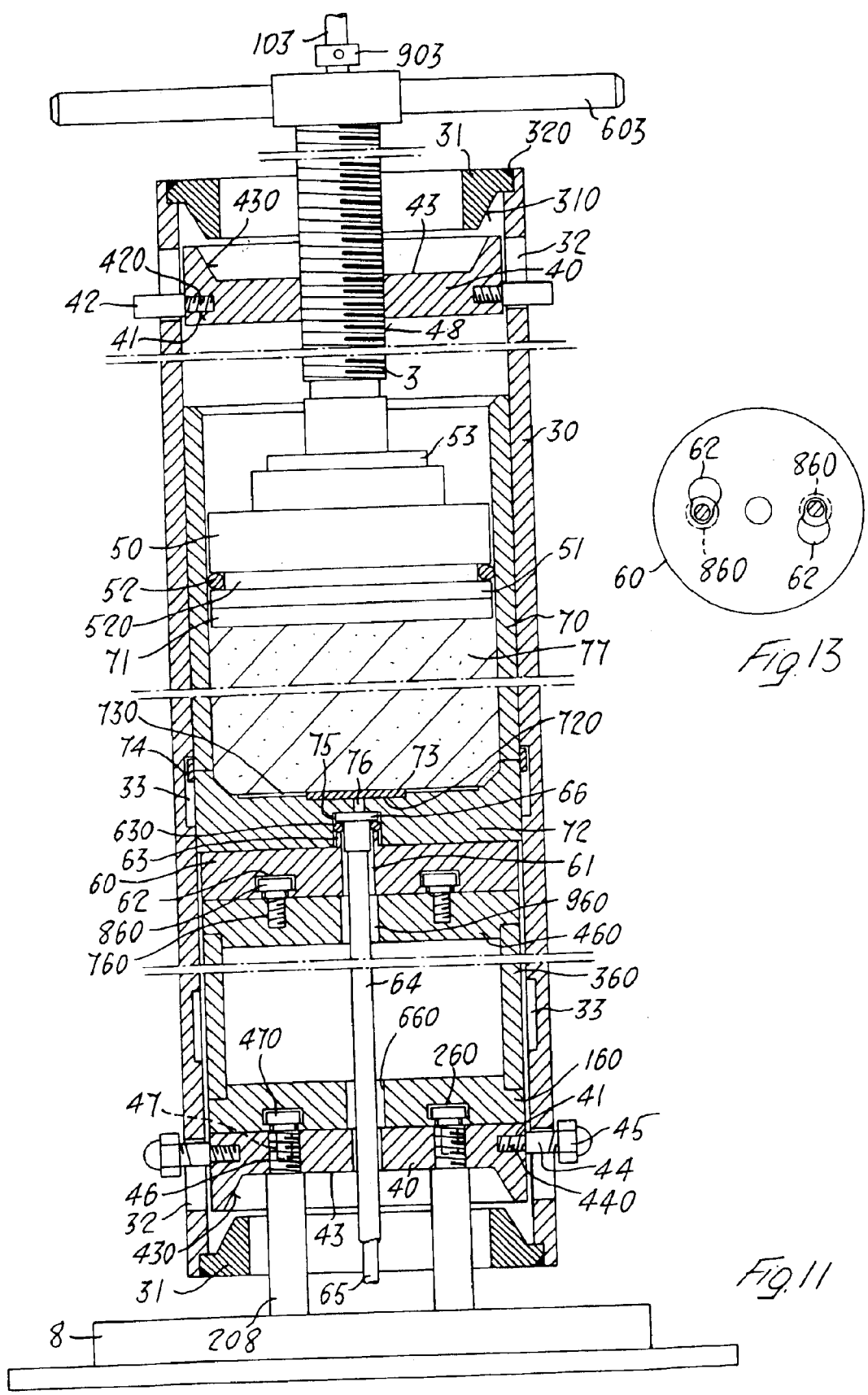

CHROMATOGRAPHIC APPARATUS

TECHNICAL FIELD OF THE INVENTION

The present invention relates to chromatographic apparatuses, and in particular to apparatuses for pressurising a removable chromatographic cartridge, such as for instance those used in c.d. flash chromatography.

BACKGROUND OF THE INVENTION

The formation of voids in the stationary portion is certainly dangerous for the working of a chromatographic column and for the accuracy of the results thus obtained. Voids can arise due both to the transport and to the packaging of the column.

It is known to introduce a chromatographic cartridge, made of polyethylene or similar material, into a biaxial compressions system, which uses two pistons acting onto the cartridge ends and provided with caps having sealing means such as O-rings. Obviously, in order to avoid radial deformations, since the material the cartridge is made of is an easily deformable plastic material, the cartridge body is fitted into a cylindrical housing, which must obviously have minimum clearances. This arrangement, however, is related to a drawback, i.e. it is extremely difficult to take the cartridge out of the housing after its use. Moreover, the sealing means used can shrink, swell and there-fore alter the working of the cartridge.

According to U.S. Pat. No. 5,601,708, another possible solution consists in carrying out a pressurized chamber around the cartridge, which prevents its radial dilatation and therefore is an obstacle to the formation of voids. This system is efficient but extremely expensive, since a pressurized chamber with suitable size should be carried out for each cartridge height; moreover, pressure needs to be efficiently controlled so as to avoid the introflexion of said cartridge.

Both systems mentioned above are characterized by the application of a pressure, axially in the first case and radially in the second one, and in both cases passive control means are provided for the unused pressure component, the cylindrical housing in the first case and the caps at the ends of the pressurized chamber in the second case.

SUMMARY OF THE INVENTION

The present invention therefore aims at providing an apparatus for pressurizing a removable chromatographic cartridge, which allows to apply pressure to said cartridge in the simplest and most homogenous way; a further aim consists in providing an apparatus that can be used with cartridges having different heights and the same section.

The object of the present invention is therefore an apparatus for pressurizing a removable chromatographic cartridge, comprising radial pressure means acting onto the side surface of said chromatographic cartridge, and axial pressure means acting onto the ends of the latter, said pressure means acting axially and radially being simultaneously active and closely related as far as their respective actuating means are concerned.

Said pressure means can comprise a hollow tubular element, preferably with a cylindrical shape, having an inner diameter that is substantially the same as the one of the cartridge.

In an embodiment said hollow tubular element comprises at least two shells substantially having the shape of a hollow cylindrical sector and complementary one to the other, and said axial pressure means comprise piston-shaped means arranged on the ends of said cartridge.

Advantageously, the actuating means of said radial pressure means and of said axial pressure means are mechanical.

BRIEF DESCRIPTION OF THE DRAWINGS

Further advantages and characteristics of the apparatus according to the present invention will be evident from the following description of some embodiments of the latter, carried out as mere non-limiting examples, with reference to the enclosed drawing tables, in which:

FIG. 11 is a view in longitudinal section of a second embodiment of the apparatus according to the present invention;

FIG. 13 is a plan view of a detail of the apparatus shown in FIG. 11.

DESCRIPTION OF SOME PREFERRED EMBODIMENTS OF THE INVENTION

Figure 1:
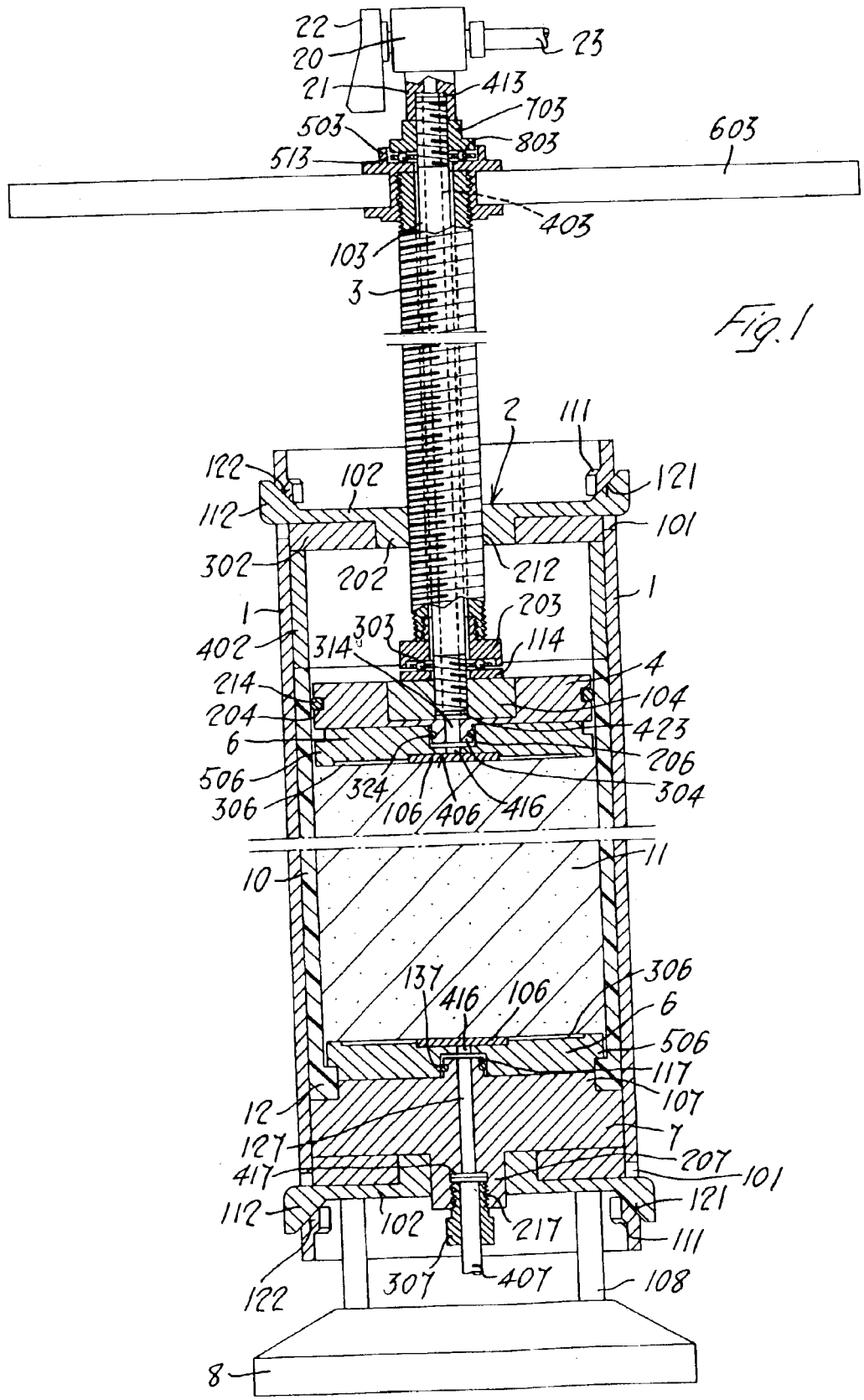
FIG. 1 is a view in longitudinal section of a first embodiment of the apparatus according to the present invention.

FIG. 1 shows the apparatus according to the present invention; the chromatographic cartridge 10 containing the stationary portion 11 is introduced into the apparatus consisting of two half-cylindrical shells 1, which are symmetrical with respect to a plane crossing the longitudinal axis of said apparatus, and are provided near their ends with a series of openings 101, on whose respective edges facing the end of the shells 1 a swelling 111 is obtained on the inner surface of the wall of said shells. The heads 112 of the radial arms 102 of a spider 2 are fitted into the openings 101; said heads 112 are provided with an inclined wall 122 cooperating with the inclined edge 121 of said openings 101.

The spider 2 has in its central body a bushing 202 provided with a threaded axial hole 212 coupling with the threaded rod 3; the bushing 202 is fitted into the bottom 302 whose section is substantially the same as the one of cartridge 10. The surface of said bottom 302 facing said cartridge 10 is in contact on its peripheral edge with the adapter 402, i.e. a cylindrical tubular element whose section corresponds to the one of the cartridge 10. The duct 103, preferably a steel tube, is fitted into the rod 3, which duct contains in its turn a Teflon tube 403 in which the eluant flows. On the opposite end with respect to the one facing the cartridge 10, the threaded rod is provided with the handle 603, mounted onto the rod through the ring nut 503; from the top of the threaded rod protrudes the duct 103, which is coupled with the fitting 21 of the valve 20 regulating the flow of eluant to the cartridge, provided with the tap 22, and connected to the intake duct 23. The tube 403 is blocked between duct 103 and fitting 21 by means of the front sealing means 413. In the portion of ring nut facing the valve 2 is obtained a ring-shaped seat housing a collar bearing 803, blocked on the opposite surface by the bushing 703.

On the end facing the cartridge 10 the duct 103 is coupled with the bushing 104 fitted into the piston 4; the rod is in its turn connected to the case 203. The thrust ball bearing 303 is placed between the ring-shaped plate 114 protruding from the surface of the bushing 104 and the inner wall of the case 203 facing the latter. The skirt of the piston 4 has a ring-shaped groove 204, into which sealing means 214 are introduced, in the case shown an O-ring, in contact with the inner surface of the side wall of the cartridge 10. On the opposite side with respect to the one connected to the threaded rod 3, the piston 4 has an axial tang 304 containing the axial through hole 314, which communicates with the end of the duct 103, where the end of the tube 403, provided with front sealing means 423, ends. The side wall of the tang 304 is provided with sealing means 324.

Between the stationary portion 11 of the cartridge 10 and the piston 4 is placed the support plate 6, which has an axial cavity 206 facing said piston 4, into which the aforesaid tang 304 is fitted, and an axial hollow 406 housing a porous separator 106, usually known as frit, said hollow 406 communicating with said cavity 206 thanks to the axial through hole 416. The edge of said hollow 406 is the starting point of a plurality of radial grooves 306. On the opposite end of the cartridge 10 the stationary portion 11 is in contact with another support plate 6, wholly similar to the one previously described, whose axial flange 506 abuts against the flange 12 axially protruding inside from the side wall of the cartridge 10.

The block 7 has a central piston-shaped portion 107, which is introduced into the opening defined by the flange 12 of the cartridge 10. The piston 107 is equipped with a tang 117 axially protruding and provided on its side wall with the sealing means 137, which tang fits into the cavity 206 of the support plate 6 placed on the bottom of the cartridge 10. The block 7 is axially crossed by the channel 127, which opens on one end onto the tang 117, and on the other one onto the bottom of the cavity 217 axially formed within the hub 207 fitted into the bushing 202 of the spider 2. The cavity 217 contains the fitting 307, which seals with the front sealing means 417 the eluant outlet tube 407 starting from the cartridge 10. The spider 2 is wholly similar to the one placed on the opposite end of the apparatus, and the heads 112 of its arms 102 are also filed into the openings 101 formed on this end of the shells 1. The apparatus rests on the base 8, which is connected to the arms 102 of the spider 2 by means of the uprights 108.

Figure 2:
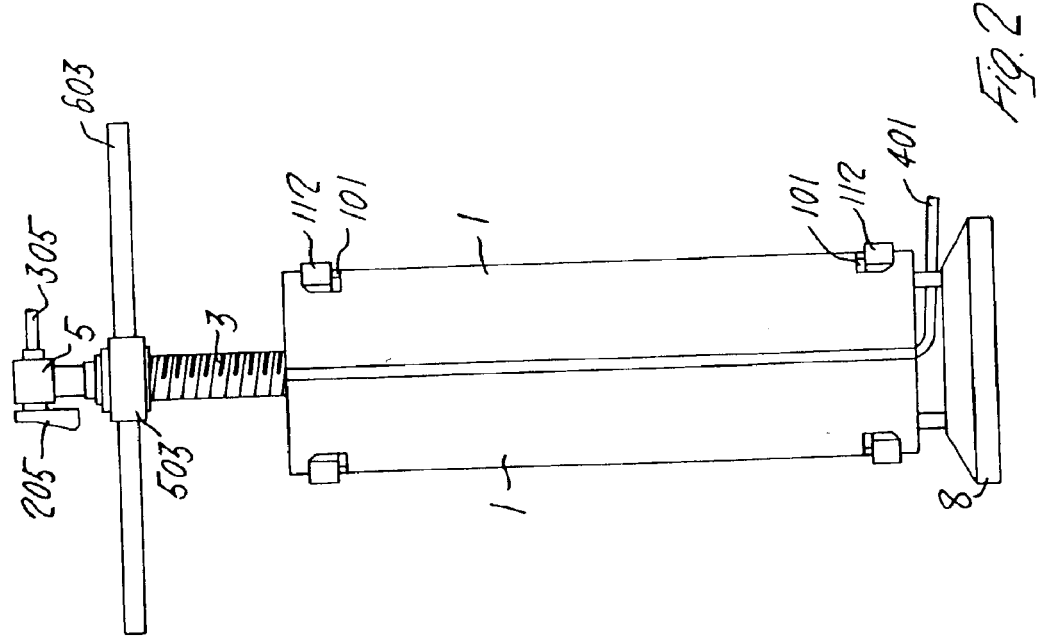
FIG. 2 is a view in side elevation of the apparatus of FIG. 1.

In FIG. 2 the apparatus according to the invention is shown in side elevation; the same elements are provided with the same references. The figure shows in further detail the two half-cylindrical shells 1 enclosing the cartridge, and the arrangements of the openings 101, with the heads 112 of the spider 2, near both ends of said shells.

Figure 3:
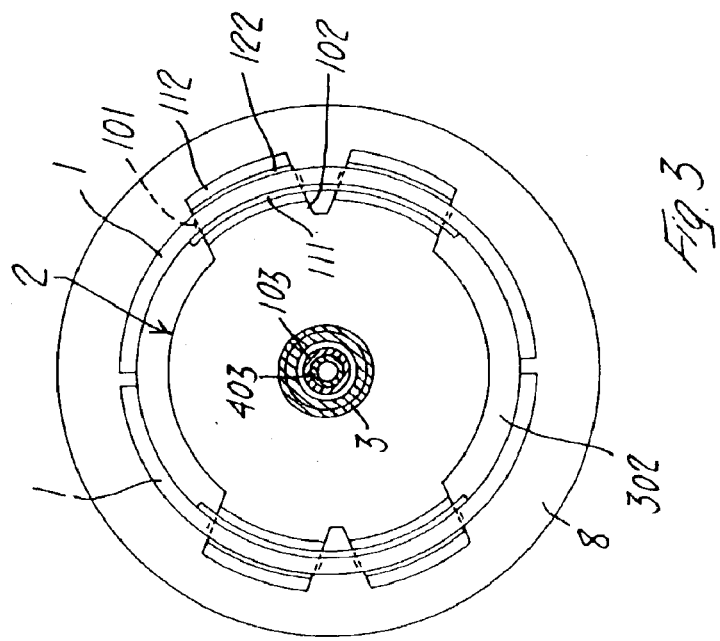
FIG. 3 is a plan view from above of the apparatus of FIG. 1.

FIG. 3 shows in further detail the arrangement of the arms 102 of the spider 2, and of the openings 101 in the shells 1; as is evident from the figure, the spider 2 has two pairs of arms 102 that are symmetrical with respect to the central axis of the spider, both arms of each pair being separated by a smaller angle than the one separating them from the adjacent arm of the opposed pair. In the specific case, an angle of 45° is included between the axes of both arms 102 of each pair; the angle between the axis of an arm of a pair and the one of the nearer arm of the other pair is therefore of 135° C. As a consequence, the openings 101 on the shells are angularly spaced accordingly.

Figure 6:
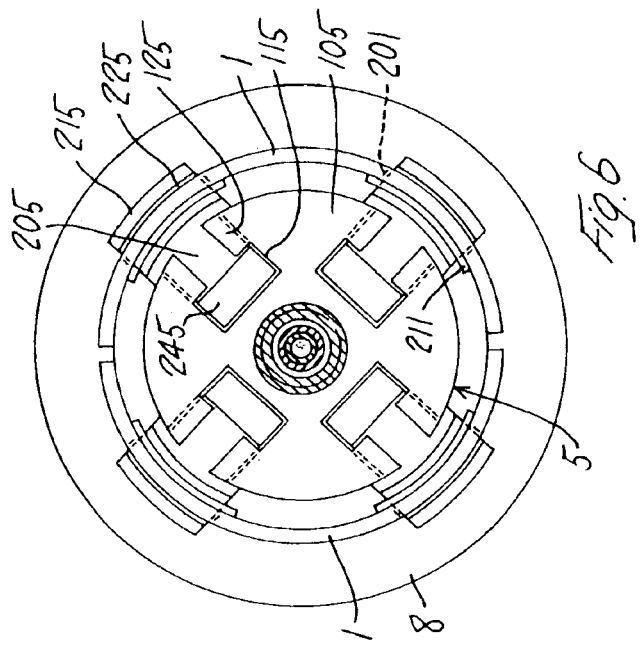
FIG. 6 is a view wholly similar to the one in FIG. 4, after assembly.
Figure 7:
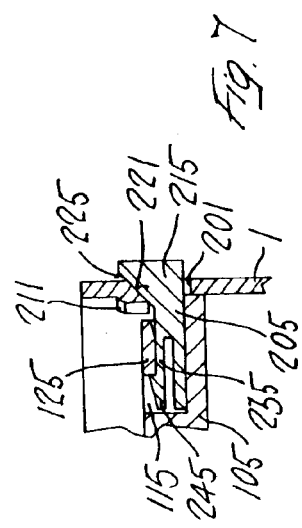
FIG. 7 is a sectioned detail along line VII—VII of FIG. 6.
Figure 4:
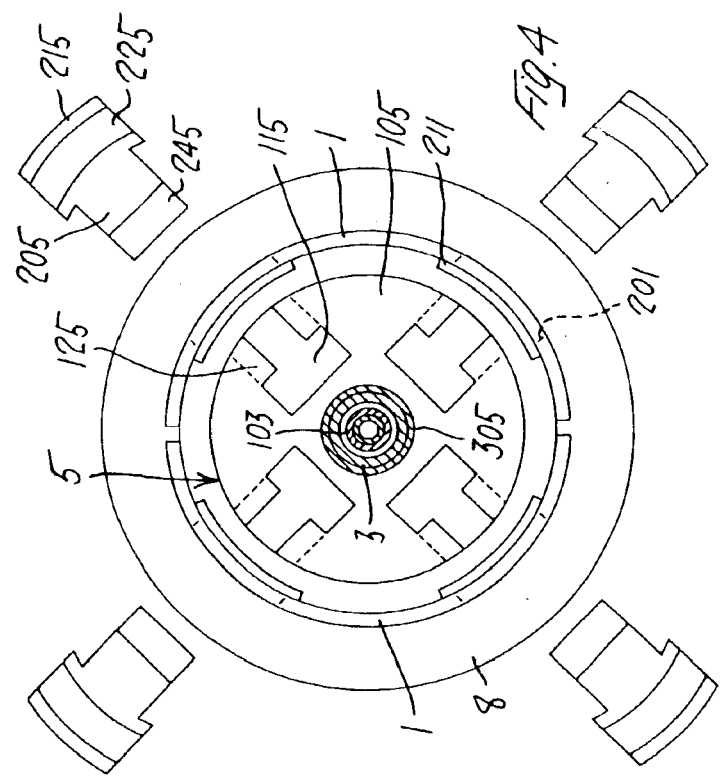
FIG. 4 is a view wholly similar to the one in FIG. 3 of a first execution variant of the apparatus according to the present invention, during assembly.
Figure 5:
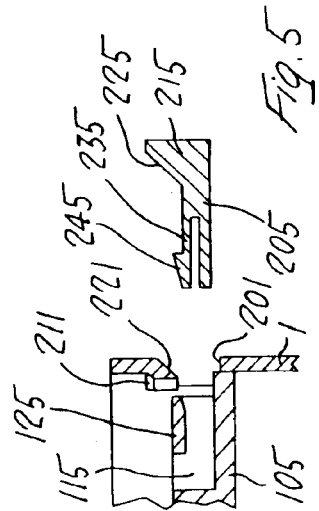
FIG. 5 is a sectioned detail along line V—V of FIG. 4.

FIG. 4 shows a first execution variant of the present invention; the spider 5 consists in this case of the plate 105 containing, at the same angular distance one with respect to the other, the four radial cavities 115, which have on their upper side edges the fins 125. Said cavities have to house the arms 205 provided with the heads 215 on which the inclined planes 225 are formed. The shells 1 have the openings 201 placed at the same angular distance one to the other and provided on the inner wall of said shells 1 with the swellings 211. From the detail shown in FIG. 5 it can be inferred that the opposite end of each arm 205 with respect to the one with the head 215 is provided with an elastic border 235 having on its free end a saw-toothed relief 245, cooperating with the fins 125 of the cavity 115 containing said arm 205, as can be inferred from FIGS. 6 and 7, which show the arrangement of the spider 5 after the introduction of the arms 205 into their respective cavities 115.

Figure 8:
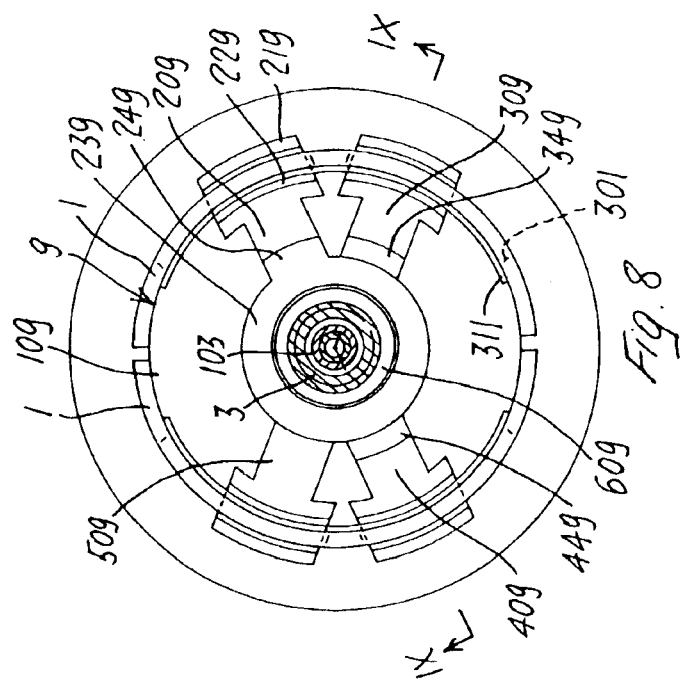
FIG. 8 is a view wholly similar to the one in FIG. 3 of a second execution variant of the apparatus according to the present invention, during assembly.

FIG. 8 shows a second embodiment form of the present invention; the spider 9, shown during assembly into the apparatus according to the invention, comprises a circular plate 109, axially provided with a hollow hub 609, which is coupled with the threaded rod 3 as previously described. The arms 209, 309, 409 and 509 are each provided on the end facing the shells 1 with the heads 219, 319, 419 and 519 having their respective inclined planes 229, 329, 429 and 529. On the opposite end each arm is provided with a ring, the figure shows only the ring 239 of the arm 209, mounted turnably onto the hub 609. The shells 1 are here provided with the openings 301, which have on the edge facing the end of said shells the swellings 311.

Figure 10:
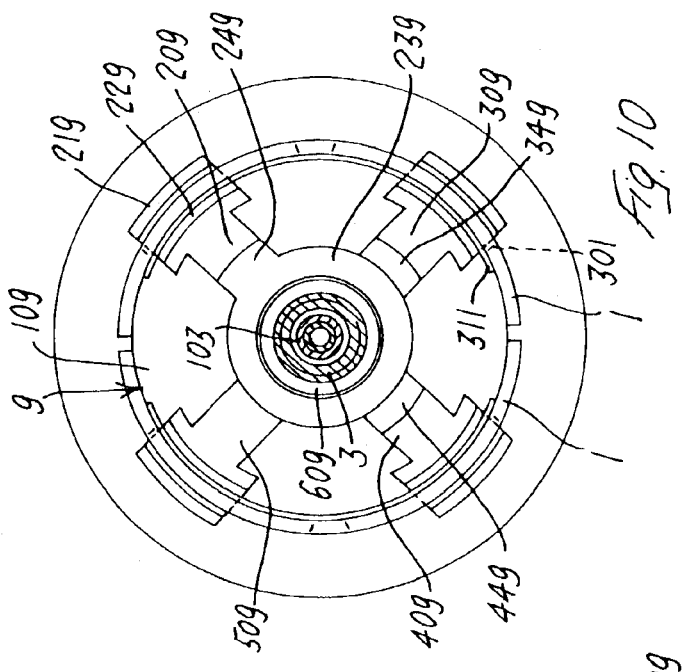
FIG. 10 is a view wholly similar to the one in FIG. 8, after assembly.
Figure 9:
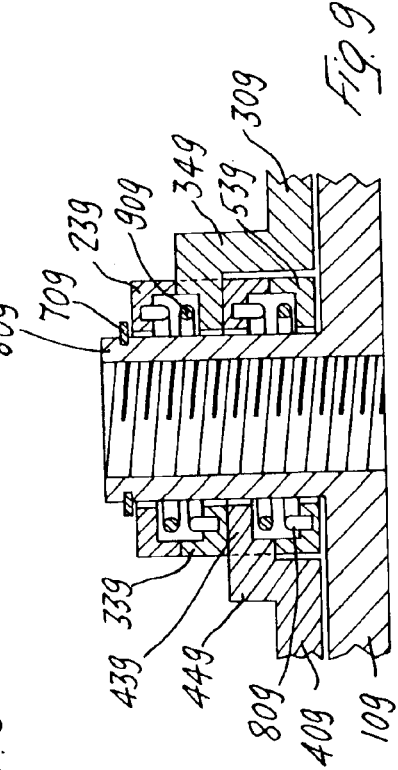
FIG. 9 is a sectioned detail along line IX—IX of FIG. 8.

FIG. 9 shows an enlarged section of a detail of FIG. 8 along line IX—IX. As is evident from the figure, the ring 239 of the arm 209 is hollow, its concavity facing the plate 109 of the spider 9. Conversely, the ring 339 below is provided with a hollow facing said ring 239; the cavity thus obtained houses the helical spring 709, fastened on one end to the ring 239 and on the other end to the ring 339. So as to connect to the ring 339, the arm 309 is provided with an angulated portion 349, and in the same way all the other arms, save for arm 509 whose ring lies on the plane of the plate 109, are provided with said angulated portion. Also the ring 439 of the arm 409 and the ring 539 of the arm 509 are connected one to the other by the spring 809 housed in the cavity included between said rings. In FIG. 10 the spider 9 is in operating position, and the arms 209, 309, 409 and 509 are placed at the same angular distance one with respect to the other.

In FIG. 11 is shown an apparatus according to a second embodiment of the present invention. The two shells 30, similar to the shells 1 previously described, are provided at both their ends with the flanges 31, radially projecting inside the apparatus, connected to the respective shell 30 by means of the welding 320 and provided with the axially protruding tapered surface 310. The tapered surface 310 cooperates with the tapered peripheral walls 430 of the cavity 43 of the plate members 40, formed on the side of each of the said plate members 40 facing the ends of the said shells 30. The plate member 40 connected to the uprights 208 of the base 8 is provided with radial threaded recesses 41 in which are fitted the threaded portions 440 of the pins 44. The said pins 44 are inserted in the slots 32 formed in the shells 30; the end of each pin 44 is screwed with a nut 45. The other plate member 40, placed at the opposite end of the apparatus, is provided with a threaded axial through hole 48, cooperating with the threaded rod 3. Also this latter plate member 40 is provided with two radial threaded recesses 41 in which are fitted the threaded portions of two projecting pins 42; the said pins are inserted in the slots 32 formed in the shells 30.

The chromatographic cartridge 70 is introduced into the shells 30; the stationary portion 77 is compressed between the support plate 71, which is in contact with the piston assembly 50-51 provided with the collar bearing 52 placed in the seat 510, and the support plate 72, which is coupled with the base 60. The base 60 is provided with an axial tang 63, which is centrally bored with an axial hole 61, the said axial tang being inserted in an axial cavity 75 formed in the support plate 72, and communicating with the hollow 720 in which is housed the frit 73 via a duct 76. Tight means 630 are placed between the peripheral edge of the tang 63 and the flanged head 66 of a duct 64 in which is placed the tube 65. The cartridge 70 is provided at the end connected with the support plate 72, with a radial projecting rim 74; the said rim 74 is inserted in the annular groove 33 formed on the inner face of both shells 30.

The base 60 is in its turn supported by the tubular spacing means 360, having an upper wall 460 from which protrude two bolts 860, fitted in the threaded holes 760, and a bottom wall 160, provided with two cavities 260, cooperating with the bolts 470 protruding from the plate 40. The bolts 860 of the upper wall 460 are inserted into the cavities 62 formed in the base 60. Both upper and bottom walls 460, 160 are respectively provided with axial holes 960, 660; the duct 64 passes through the said holes 960, 660. As it is shown in FIG. 13, the bolts 860 and the cavities 62 give rise to a twist-lock connection (bolts 470 and cavities 260 act in the same way).

Figure 12:
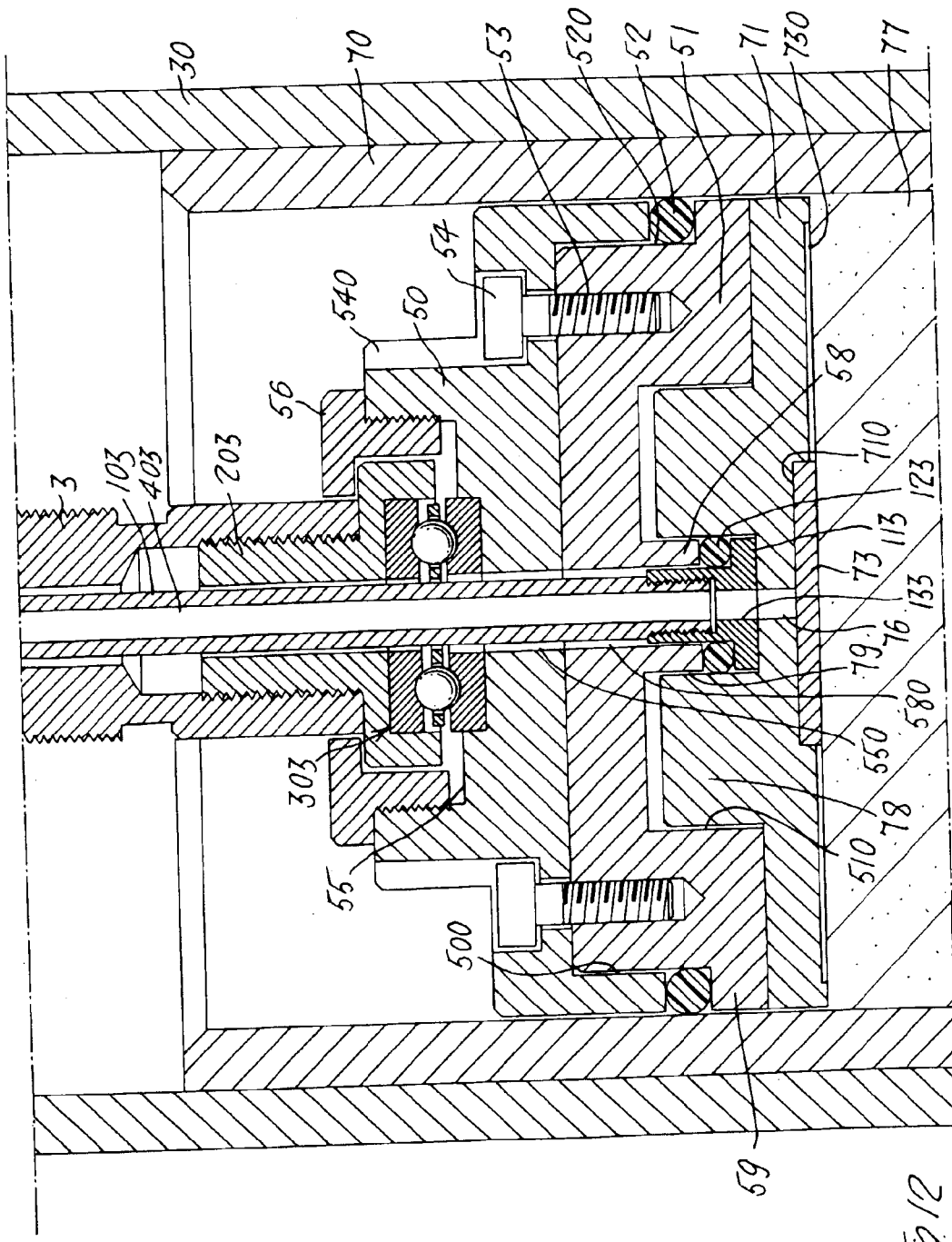
FIG. 12 is an enlarged longitudinal sectional view of a detail of FIG. 11.

In the FIG. 12 is shown a detail of FIG. 11, in longitudinal section; the piston assembly, slidably inserted into the cartridge 70, comprises an upper cup-shaped body 50, and a lower cup-shaped body 51. By the insertion of the body 51 into the cavity 500 of the cup-shaped body 50 is thus obtained a seat 520 in which can be fitted the collar bearing 52; the bearing 52 is compressed between the peripheral edge of the body 50 and the flange 59 projecting outside of the body 51. The two bodies 50, 51 are mutually connected by means of the bolts 54 inserted into the through holes 540 formed in the body 50 and in the threaded holes 53 of the body 51. The said connection is realised in a such way as to leave a certain axial gap between the two cup-shaped bodies 50, 51.

In the portion of the cup-shaped body 50 facing the rod 3 is formed an axial cavity 55 having threaded lateral walls coupled with a locknut 56, which engages the case 203. The thrust ball bearing 303 is placed between the bottom wall of the cavity 55 and the inner wall of the case 203 facing the latter. The cup-shaped body 51 is provided with an axial cavity facing the support plate 71 of the cartridge 70; in the said cavity is fitted an axial tang 78 projecting from the said support plate 71. The said tang 78 has in its centre an axial recess 79 which is coupled with an axial projection 58 protruding from the bottom wall of the cavity 510 of the body 51. The duct 103 passes through the axial hole 550 of the body 50 and the axial hole 580 of the body 51, and it is provided, at its free end exiting from the projection 58, with a flanged head 113, provided with the through hole 133, which head 113 compresses the collar bearing 123 against the edge of the said projection 58. The recess 79 of the support plate 71 communicates with the hollow 710 in which is housed the frit 73 via a conduit 76.

The working of the apparatus according to the present invention will be evident from the following. Referring to the embodiment shown in FIGS. 1 to 3, the chromatographic cartridge 10 is equipped with the stationary portion 11 fitted into its cylindrical tubular body, and with the two support plates 6 of the frits 106. The end of the cartridge 10 having the flange 12 is arranged on the portion 107 of the block 7, and the tang 117 is fitted into the cavity 206 of the corresponding plate 6. On the opposite end of the cartridge is introduced into the body of the latter the piston 4, whose tang 304 couples with the cavity 206 of the other plate 6. Between the bottom 302 of the spider 2 coupled with the threaded rod 3 and the end of the cartridge 10 has been introduced the spacer 404, which can alternatively be obtained as one piece with said bottom 302. The following step consists in fitting the heads 112 of the arms 102 of the spiders 2 into the openings 101 made in the shells 1; after thus assembling the apparatus, by turning the threaded rod 3 by means of the handle 603, the piston 4 comes down into the cartridge 10. Simultaneously, the spider 2, coupled with the threaded rod 3 by means of the bushing 202, is pushed upwards; this moving makes the inclined planes 122 of the heads 112 of the arms 102 and 121 of the openings 101 reciprocally slide on both ends of the apparatus, which results in the reciprocal clamping of both shells 1.

The relation between radial and axial pressure means is therefore granted by the screw/female thread coupling between threaded rod 3 and bushing 202 of the spider 2; obviously, the rotation of the actuating means of the piston 4 should not result in a rotation of the latter within cartridge 10. To this purpose sliding means are used, such as the collar bearing 303 placed on the end of the rod 3 facing said piston 4; similarly, also the rotation of duct 103, containing the eluant intake tube 403, is avoided by arranging the thrust bearing 803 on the ring nut 503 of the handle 603.

Advantageously, the peripheral edge of the openings 101 facing the end of said shells has a swelling 111, which enables to increase the sliding surface 121 cooperating with the inclined planes 122 formed on the heads 112 of the arms 102 of the spiders 2. The inclination of said planes 122, and therefore of the surfaces 121, is here of 45°, but a different inclination can be used according to the relation to be established between axial and radial pressure, in accordance with the specific structural features of the cartridges that will be used in the apparatus.

The pressure exerted onto the cartridge 10 is spread homogenously both on the side surface and on its ends; with respect to means used in devices known at the state of the art it should be pointed out that there is a close relation between the means exerting both pressures. As a matter of fact, a given penetration of the piston 4 into the cartridge 10 corresponds to a given sliding of the inclined planes, thus resulting in the shells 1 reciprocally approaching. This kind of relation was not to be found in any of the known systems, and it allows to avoid structural deformations of the cartridge due to loads, which would nullify the positive effects of pressure. The pressure means used in the embodiments shown and described are mechanical, although wholly analogous results could be obtained by using other actuating means; for instance pneumatic, oleo-pneumatic or similar pressure means could be used.

The choice of spider-shaped means acting on both shells 1 derives from the fact that such means allow in an extremely simple way to ensure a distribution as symmetrical as possible to the loads applied onto the cartridge. In the embodiment of FIGS. 1 and 2, the spider 2 is made as one piece and the arms are arranged in pairs placed symmetrically one to the other. This kind of arrangement is a compromise between the ideal situation, in which the arms have to be at the same angular distance, and the need for an easy introduction of the arms into the openings 101 of the shells 1.

Conversely, the ideal arrangement is obtained according to the execution variant shown in FIGS. 4 to 7; in this case the arms 205 can be fitted with a release mechanism into the plate 105 of the spider 5, which allows to mount them from outside with respect to the shells 1, thus avoiding the problem existing had the spider 2 been carried out as one piece. The advantage resulting therefrom, beyond an improved load distribution thanks to the manifest higher symmetry of the structure, is an easier assembly of the apparatus, since the heads need no more to be fitted into the openings of the shells 1.

Another alternative solution that represents a good compromise between easy assembly and good radial distribution of pressure loads is the one provided by the embodiment form shown in FIGS. 8 to 10 of the enclosed drawings. As a matter of fact, the arms of the spider 9 can be introduced into the openings 301 exactly as those of the spider 2, but after the introduction they can reach a position in which they are at the same angular distance. Obviously, the openings 301 are here broader than those used in the embodiment form previously described, so as to allow the arms to make their movement. The elastic return means 709 and 809 place the arms in the position shown in FIG. 10, and during assembly the two pairs of arms must be placed close to one another so as to enable their introduction into the openings 301.

In general, the openings on the shells 1 should be broad enough to enable the heads of the arms of the spiders to be placed therein, but should at the same time be not so broad as to damage the good load distribution on the walls of the shells 1.

In the second embodiment of the invention, shown in FIGS. 11 to 13, the achieved solution allows the use of inclined surfaces for the means pushing the shells 30 one toward the other and at the same time overcomes the problems relating to the arrangement of the arms of the spider-shaped means. The tapered surface 310 of the flanges 31 and the tapered wall 430 of the cavity 43 of the plate 40 cooperate almost in the same way as the inclined surface formed on the ends of the arms of the spider and on the edges of the openings of the shells; the distribution of the charge and the close relation with the actuation of the piston, owing to the coupling between the plate 40 and the rod 3, are hardly maintained.

Moreover, these actuating means are much more easy to be realised and to be operated; from the constructive point of view, it is only necessary to weld, on both ends of a tube, a flange of the kind shown in FIG. 11, and then to perform a longitudinal cut of the same tube; similarly, the plate 40 is a circular plate in which a tapered cavity has to be realised. The pins 42 have the mere function of preventing the shell to rotate while the rod 3 is turning; the pins 44 provided with the nuts 45 have the additional feature of keeping the shell 30 connected to the base 8 even after the extraction of the piston from the cartridge.

The apparatus according to the present invention further allows, differently from those known at the state of the art, to use cartridges having a different length but the same diameter. As shown in FIG. 1, the presence of a spacer 404 allows the apparatus to work with a column having a given length, since said spacer balances the distribution of loads applied by the shells 1; a further advantage obtained thanks to said spacer consists in an easier extraction of the piston 4 from the cartridge 10, since the peripheral edge of the spacer 404 is led into contact against the end of the cartridge 10 when the rod is taken out.

The cartridges 10 used in the apparatus according to the invention are preferably equipped with support plates 6 for the frits 106; said plates 6 are carried out so as to minimize the size of the frit 106, which is normally made of materials with high manufacturing and processing costs, without reducing the efficient distribution of the eluant in the stationary portion. That is why the frit 106 is housed in a hollow 406 communicating with the grooves 306 obtained on the support plate; the eluant, after passing through the frit 106, will spread in the grooves on the whole section of the cartridge 10. Analogously, on the outlet end of the edge the whole section of the stationary portion 11 will spread the eluant on the plate 6, and the grooves 306 will lead said eluant towards the frit 106 and then to the outlet channel 127. Preferably, the support plate 6 arranged on the outlet end of the cartridge 10, i.e. the one whose cavity 206 is coupled with the tang 117 of the piston-shaped portion 107 of the block 7, shall be welded to the flange 12 of said cartridge.

The cartridge 70 shown in FIG. 11 has still another advantageous feature; in fact it is provided with the rim 74 which prevents, in cooperation with the groove 33 formed on the inner surface of the shells 30, the extraction of the cartridge together with the piston. The said rim 74 can consist in the same weld bead obtained after the welding of the support plate 72 to the cartridge 70. The shells 30 are provided with two or more annular grooves 33, so as to allow the use of cartridges of different size.

In the embodiment shown in FIGS. 11 and 13, the spacing means 360 are placed below the support plate 72 of the cartridge 70. This arrangement is allowed by virtue of the cooperation between the above described rim 74 and the groove 33. Advantageously, the spacing means can be stably connected to at one end the plate 40, by means of the bolts 470 projecting from the plate 40 and of the cavities 260 formed in the lower wall 160 of the spacing means 360 and to the base 6, and at the other end to the base 60, using the same kind of connection between the bolts 860 and cavities 62.

A further advantage of the apparatus according to the present invention consists in positioning the sealing means on the parts which do not undergo wear-and-tear; this choice allows to obtain cheaper chromatographic cartridges, since the O-rings used for sealing the piston are made of a material that should be able to be resistant against a large number of substances, and are therefore extremely expensive. This choice further simplifies the manufacturing of the support plates and reduces their operating cost.

Consequently to what is stated above, the embodiment of the FIGS. 11 and 12 provides a further improvement; in fact, the material used for producing the O-rings used for sealing the piston is normally relatively stiff, and the corresponding loss in elastic properties can cause the increase the possibility of leakage in the assembly piston/cartridge. Accordingly, a piston realised as shown in FIG. 12 can easily overcome these drawbacks; the collar bearing 52 is in fact compressed between the edge of cup-shaped body 50 and the flange 59 of the body 51. From one hand, this type of compression prevents any leakage, and from the other hand the structure of the piston allows the use of a bearing having poor elastic properties, since the introduction of the same bearing in the seat 520 is very easy to be performed.

What is claimed is:

1. An apparatus for pressurizing a removable chromatographic cartridge having a side surface and ends, said apparatus comprising:

radial pressure means acting on the side surface of the chromatographic cartridge, and axial pressure means acting on the ends of the chromatographic cartridge, said radial pressure means comprising a hollow tubular element having an inner diameter that is substantially the same as the outer diameter of said chromatographic cartridge, said axial pressure means and radial pressure means being simultaneously active and actuating means for said radial pressure means and axial pressure means.

2. The apparatus according to claim 1, wherein said hollow tubular element comprises at least two pressure shells substantially having the shape of a hollow cylindrical sector, said at least two pressure shells being complementary to each other, and said axial pressure means comprise piston-shaped means arranged on the ends of said chromatographic cartridge.

3. The apparatus according to claim 2, wherein said actuating means of said pressure shells comprise two members arranged on ends of said pressure shells on planes that are substantially perpendicular to the longitudinal axis of said pressure shells, provided on their peripheral edges with suitable means pushing said shells towards the one another when said axial pressure means are actuated.

4. The apparatus according to claim 3, wherein said means pushing said shells towards one another comprise first inclined surfaces located on the peripheral edges of said members cooperating with second inclined surfaces complementary to the first inclined surfaces and arranged on the ends of said shells.

5. The apparatus according to claim 4, wherein said first inclined surfaces and said second inclined surfaces lie substantially on an average inclination plane having an inclination comprised within 15° and 45° with respect to the longitudinal axis of said shells.

6. The apparatus according to claim 4, wherein said second inclined surfaces comprise a tapered lateral surface of an inward projecting flange disposed at each end of said shells.

7. The apparatus according to claim 6, wherein said members comprise cylindrical plate means having an axial cavity facing the ends of said shells, the side wall of said cavity being tapered.

8. The apparatus according to claim 4, wherein said members comprise spider-shaped means arranged on the ends of said shells on planes that are substantially perpendicular to the longitudinal axis of said shells, and having two or more radial arms comprising free ends cooperating with walls of said shells.

9. The apparatus according to claim 8, wherein said second inclined surfaces comprise edges facing said ends of the shells of openings obtained in the walls of said shells.

10. The apparatus according to claim 9, wherein the edges of said openings comprise swellings increasing contact surface of said inclined surfaces.

11. The apparatus according to claim 3, wherein said actuating means of the piston-shaped means comprise a threaded rod coupled on one end, freely turnable provided by suitable means, with said piston-shaped means, and coupled with a threaded bushing axially disposed within said member.

12. The apparatus according to claim 11, wherein a stiff tubular element integrally connected on one end to said piston is coaxially arranged within said threaded rod.

13. The apparatus according to claim 12, wherein said piston is provided with an axial channel in fluid communication with said stiff tubular element, an eluant intake/outlet duct being provided within said stiff tubular element, and said stiff tubular element being connected on its other end to eluant intake/outlet means.

14. The apparatus according to claim 11, wherein said piston is provided with sealing means cooperating with the walls of said cartridge.

15. The apparatus according to claim 11, wherein said piston-shaped means comprises:

an upper cup-shaped body, and a lower cup-shaped body; and a seat, adapted to accommodate a collar bearing, is formed by the insertion of the lower body into the cavity of the upper cup-shaped body, said upper cup-shaped body and lower cup-shaped body being mutually connected by a connection forming an axial gap between said upper cup-shaped body and said lower cup-shaped body.

16. The apparatus according to claim 11, wherein the piston-shaped means comprise a piston-shaped portion connected to said member, said piston shaped portion communicating with eluant outlet means, and said member being arranged on uprights connected to a base.

17. The apparatus according to claim 16, wherein said piston-shaped portion is connected to said member by means of twist-lock engagement between cavities and projections formed on the mutually facing surfaces.

18. The apparatus according to claim 11, wherein said piston-shaped means are provided with an axial projecting tang having a through passage in which is inserted said stiff tubular element, an eluant intake/outlet duct being provided within said stiff tubular element, an end portion of said stiff tubular element being provided with a flanged head, and a collar bearing being placed between said flanged head and trail edge of said tang.

19. The apparatus according to claim 3, said apparatus accommodates use of at least two different sizes of cartridges, and further comprising spacing means which allow the compensation for different size cartridges.

20. The apparatus according to claim 19, wherein said spacing means comprise a tubular member, having the same section of said cartridge and placed in contact with said cartridge at its inlet end.

21. The apparatus according to claim 19, wherein said spacing means comprise a tubular member provided with an upper and a lower transverse walls, said upper and lower walls being provided with means for coupling with said piston-shaped and with said member arranged on uprights connected to a base, respectively.

22. The apparatus according to claim 1, wherein said hollow tubular element has a cylindrical shape.

23. The apparatus according to claim 1, further adapted to accommodate an outwardly extending rim of the cartridge.

* * * * *